United States Patent [19]
Abrosimov et al.

[11] Patent Number: 5,980,698
[45] Date of Patent: Nov. 9, 1999

[54] METHOD FOR VACUUM DISTILLATION OF A LIQUID PRODUCT AND AN EQUIPMENT FOR PERFORMING THEREOF

[75] Inventors: Alexandr Alexeevich Abrosimov; Alexandr Mikhailovich Kochemasov; Ivan Alexandrovich Kochergin; Valery Grigorievich Tsegelsky, all of Moscow, Russian Federation

[73] Assignee: Valery Grigorievich Tsegelsky, Moscow, Russian Federation

[21] Appl. No.: 08/776,066

[22] PCT Filed: Aug. 19, 1994

[86] PCT No.: PCT/RU94/00197

§ 371 Date: Jan. 7, 1997

§ 102(e) Date: Jan. 7, 1997

[87] PCT Pub. No.: WO96/05900

PCT Pub. Date: Feb. 29, 1996

[51] Int. Cl.⁶ .............................. B01D 3/10; B01D 3/12; C10G 7/06
[52] U.S. Cl. .......................... 203/94; 196/114; 202/182; 202/197; 202/204; 202/205; 203/98; 203/DIG. 14; 208/92; 208/100; 208/357; 208/366
[58] Field of Search ................................. 203/91, 94, 98, 203/DIG. 14, DIG. 25, 99, DIG. 19; 208/357, 366, 92, 100; 202/205, 202, 185.2, 197, 182, 204; 196/99, 114

[56] References Cited

U.S. PATENT DOCUMENTS

| | | | |
|---|---|---|---|
| 2,073,446 | 3/1937 | Ellsberg | 208/357 |
| 2,140,342 | 12/1938 | Wallis et al. | 196/114 |
| 3,579,307 | 5/1971 | Wakita et al. | |
| 3,642,384 | 2/1972 | Huse | 417/68 |
| 3,796,640 | 3/1974 | Boomer | |
| 4,144,280 | 3/1979 | Winter, III | 585/450 |
| 4,175,034 | 11/1979 | Thompson | 208/321 |
| 4,194,924 | 3/1980 | Safranko et al. | 203/DIG. 14 |
| 4,381,971 | 5/1983 | Dietrick | 203/DIG. 14 |
| 4,554,055 | 11/1985 | Rooney | |
| 4,664,786 | 5/1987 | Forte et al. | 208/356 |
| 4,695,349 | 9/1987 | Becker et al. | 203/DIG. 14 |
| 4,717,468 | 1/1988 | Funk | 208/356 |
| 5,386,872 | 2/1995 | Chang | 165/47 |

FOREIGN PATENT DOCUMENTS

| | | |
|---|---|---|
| 724149 | 3/1980 | Russian Federation . |
| 740808 | 6/1980 | Russian Federation . |
| 2048156 | 11/1995 | Russian Federation . |

OTHER PUBLICATIONS

Chemical Industry No. 8, 1991, p. 20 (468) Intensification of Processes in Chemical Technology by Zaporozheta, I.A. Aleksandrov.

K.P. Shumski "Vacuum apparatus and equipment in chemical engineering", Moscow, Mashinostroyeniye Publishers, 1974, pp. 123, 143, 153.

Petroleum Refiner Handbook. Ed. G.A. Lastovkin, Leningrad, Khimiya Publisher, 1989, p. 74.

*Primary Examiner*—Virginia Manoharan
*Attorney, Agent, or Firm*—Nath & Associates; Gary M. Nath; Harold L. Novick

[57] ABSTRACT

A method for vacuum distillation includes separation of a liquid product delivered to a reservoir under vacuum into a vapour-gaseous phase and at least one liquid fraction, withdrawal of the vapour-gaseous phase from the reservoir using a vacuum-creating device, and subsequent separation of the vapour-gaseous phase into gas and a liquid phase by condensing performed directly in the vacumm-creating device. A portion of the liquid phase is used as a fluid working medium in the vacuum-creating device.

An equipment for vacuum distillation includes a reservoir under vacuum conditions equipped with mains and a vacuum-creating device, which has an ejector, a separator and a pump, interconnected by mains.

4 Claims, 1 Drawing Sheet

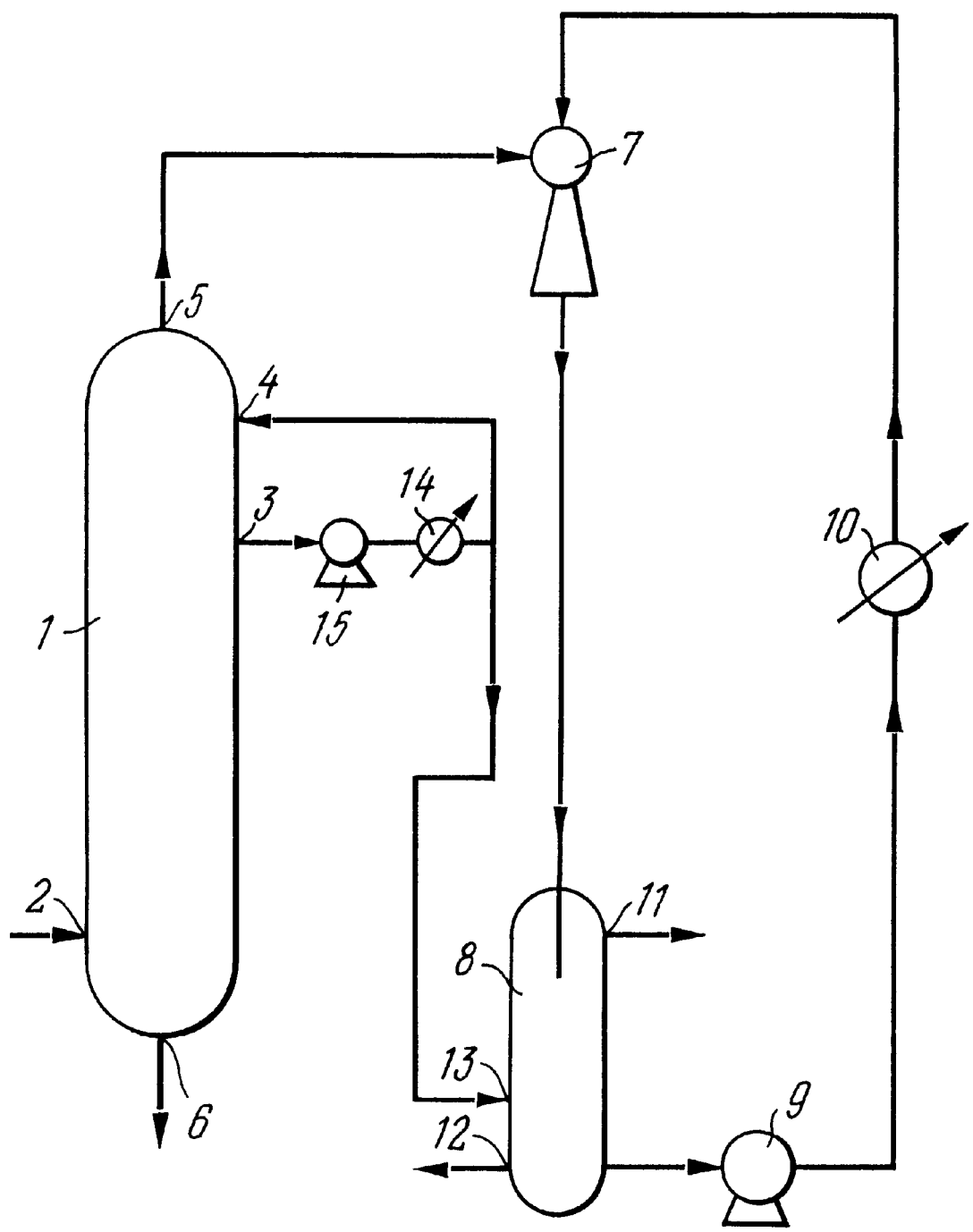

METHOD FOR VACUUM DISTILLATION OF A LIQUID PRODUCT AND AN EQUIPMENT FOR PERFORMING THEREOF

AREA OF THE INVENTION

This invention relates to a method and equipment for vacuum distillation of a liquid product, presumably of petroleum stock, and may be used in petroleum refining industry for rectification of petroleum base stock at vacuum column.

STATE OF ART

A method is known and an equipment for vacuum distillation of petroleum stock, which includes a vacuum column equipped with a side section, wherein the reduced pressure is produced using a jet blower (ejector), wherein the active (ejecting) medium used is steam (U.S. Pat. No. 2,073,446 and U.S. Pat. No. 2,140,342).

However, the defficiency of the known method and equipment is in mixing of petroleum fractions with steam and, accordingly, carrying away by steam a portion of petroleum fractions, the latter leading to contaminating of steam and to reducing the equipment efficiency.

A method is known for vacuum distillation of a liquid product which comprises feeding the latter to a reservoir under vacuum, separating the liquid product in reservoir to gases and vapours of readily volatile fractions and to at least one liquid fraction, pumping out from the upper reservoir volume the gases and vapours using a vacuum-creating apparatus through a condensing cooler, and discharging them from the latter (K. P. Shumski "Vacuum apparatus and equipment in chemical engineering", Moscow, Mashinostroyeniye Publishers, 1974, pages 123, 143, 153).

An equipment is known as well for vacuum distillation of petroleum stock which comprises a vacuum column with mains for feeding the petroleum stock and removing the liquid fraction, and a main for removing gases and vapours of easily volatile(upper) petroleum fractions from the top of the column, which is connected to a vacuum-creating apparatus (ejector-type steam pump). The mains between the top of the column and the vacuum-creating apparatus comprises a cooling condenser (Petroleum refiner Handbook. Ed. G. A. Lastovkin, Leningrad, Khimiya Publisher, 1989, page 74).

According to the known method and equipment, the vacuum value in the column is achieved using ejector-type steam pump, in which the ejecting (working) medium used is steam.

The steam mixes with petroleum vapours and decomposition gases, this resulting in contamination of steam condensate with the former products, and in removing by the steam condensate of the top petroleum fractions. Moreover, the ejector-type steam pump does not provide compressing of hydrocarbon gases which are not condensed after the cooling condenser to a pressure necessary for feeding said gases to e.g. fuel collector of petroleum refinery plant. Therefore, said gases are to be burned in flame tounges if additional compressor equipment is absent.

The condensed matter from vacuum-creating device is delivered to a settling tank wherein the petroleum product is separated from aqueous condensate. The settling tanks of said type represent obviously environment sources.

Another, shortage of the known method and equipment is in condensing of easilly volatile fractions before the vacuum-creating device in the cooling condenser, this, due to pressure differential in the latter, results either in higher pressure at the top of the column leading to reduced yield of volatile (light) products, or to the power increase provided for the vacuum-creating device.

DISCLOSURE OF THE INVENTION

The object of the given invention is a problem of creating the method and the equipment for vacuum distillation of a liquid product, which should provide intensification of vacuum distillation process by producing the closed circuit of vacumm-creating device, in order to reduce environmental pollution and to reduce power consumption along with equipment efficiency increase.

The stated problem is solved by that in the method for vacuum distillation of a liquid product, presumably petroleum based one, which method comprises feeding a liquid product to a reservoir under vacuum, separating the liquid product in the reservoir to a vapour-gaseous phase and to at least one liquid fraction, and subsequent separating the vapour-gaseous phase into a gas and liquid phase by vapour condensing, wherein the vapour-gaseous phase is discharged from the reservoir using a vacuum-creating device, vapour condensing is carried out directly in the vacuum-creating device, and a portion of liquid phase is used as a fluid working medium for vacuum-creating device along with preliminary removing therefrom the heat excess.

It is preferable to refresh the fluid working medium by adding thereto at least a portion of the liqid fraction from the reservoir.

In the equipment for vacuum distillation, presumably of petroleum stock, which equipment comprises a reservoir under vacuum conditions having attached mains for feeding a liquid product and for discharging at least one liquid fraction, and a main for removing vapour-gaseous phase which connect the upper reservoir portion with vacuum-creating device, the vacuum-creating device includes an ejector, separator and pump,interconnected by mains, wherein the gas inlet of the ejector is connected with the mains for vapour-gaseous phase discharge, the liquid inlet of the ejector is connected to the separator outlet, and the liquid outlet of the separator is connected to the pump inlet.

It is advisable to place the cooler at the mains between the liquid inlet of the ejector and the liquid outlet of separator, this enabling to remove heat excess from the liquid phase.

The connection of the additional separator inlet with the mains for removing fluid fraction from the reservoir provides refreshing of the fluid working medium with liquid fraction drawn from the reservoir into the closed circuit of the vacuum-creating device.

The suggested method for vacuum distillation of a liquid product and the equipment provide effective removal of vapour-gaseous phase from the upper portion of the reservoir followed with its condensing both in the flow part of ejector, and in the mains after the ejector. The uncondensed gases (hydrocarbon gases in the case of petroleum refinery) are simultaneously compressed to the pressure required for a user. The latter provides delivering from the separator of a hydrocarbon gas under a pressure which may be used for technology requirements, and the excess of the liquid phase may be delivered as an intermediate product for further technological processing. In contrast to the analogous art, the claimed method does not include mixing of the top petroleum fractions with water and expeling of condensate and hydrocarbon gases (in the case of petroleum refining) to the environment. Thus, the claimed method is ecologically pure one.

Moreover, the claimed method makes it possible not to use the cooling condenser for vapours of said light petroleum fractions at the mains which connects the upper portion of the reservoir with the vacuum-creating device, because condensation of the light petroleum fractions' vapours takes place in the ejector. The claimed method provides as well reducing of the outer circulation reflux rate of the column top, the latter resulting in reduction of pressure difference there, and finally leads to pressure reducing in the bottom of the column, this providing yield increase for the low-boiling (light) products of vacuum distillation.

Such a method and construction execution of the equipment for vacuum distillation of a liquid product provides substantive decrease in environment contamination, decreasing power consumption and, accordingly,increasing in the equipment output.

BRIEF DESCRIPTION OF DRAWING

The invention is further demonstrated by the detailed description of its fulfilment example with reference to the enclosed drawing, wherein the scheme is presented of the equipment for vacuum distillation of a liquid product.

The Preferable Version of the Invention's Achievement

The claimed equipment contains the fractionating vacuum column 1 equipped with mains 2 for feeding heated liquid product (e.g. petroleum stock), mains 3 for liquid fraction output, mains 4 of the external circulation reflux, mains 5 for output of vapour-gaseous phase and mains 6 for output of the column bottoms. The mains 5 connects the column top 1 with the liquid-gaseous ejector 7 which is connected by mains with separator 8 and pump 9. The ejector 7, separator 8 and pump 9 represent the vacuum-creating device, wherein the gas input of the ejector 7 is connected with the mains 5 of vapour-gaseous phase output, the liquid input of ejector 7 is connected with the output of the pump 9, the output of ejector is connected with the input of separator 8, and the liquid output of separator 8 is connected with the input of the pump 9.

The cooler 10 is mounted at the mains between the liquid input of the ejector 7 and the liquid output of separator 8. The separator 8 is connected by the mains 11 with the consumer's fuel system, and by the mains 12 with the petroleum product receiver (the latter are not shown on the drawing). The additional input of the separator 8 is connected with the mains 3 for discharge of liquid fraction at the column 1 by means of the mains 13 used for additional feeding of the vacuum-creating device with a liquid fraction from the column. The cooler 14 and the pump 15 are mounted at the mains 3 used for additional feeding of the vacuum-creating device. The cooler 14 output is connected by mains 4 of the outer circulating reflux with the column 1.

The performance of the suggested equipment for vacuum distillation of a liquid product is carried out as follows.

The heated liquid product (petroleum stock in the case of petroleum distillation) is fed to the column 1 under a pressure of 10–60 mm Hg via the input mains 2. The liquid fraction (vacuum gas oil) is discharged via the mains 3 which passes through the pump 15, is cooled in the cooler 14, and is then divided into two flows, one of which via the mains 4 is directed to the external circulating reflux of the upper column portion, and the second flow is directed via the mains 13 and through an additional input to the separator 8 of the vacuum-creating device. The liquid phase is gradually saturated with decomposition gases (hydrocarbon gases) evacuated from the upper column portion, this reducing vacuum extent in the column due to evolution of said gases in the ejector nozzle. The latter causes energy consumption at the liquid phase pump derived of the vacuum-creating device. Therefore, in order to produce better vacuum, and to reduce power consumption in creating the latter, the liquid phase circulating in the vacuum-creating device is gradually refreshed using the liquid fraction coming from the column to the closed circuit of the vacuum-creating device.

From the top column portion, via the mains 5, the vapour-gaseous phase is discharged, which is sucked off by the liquid-gas ejector 7 by means of the energy of liquid phase recycling in the closed circuit due to the pump 9. In the cooler 10 of the vacuum-creating device, the excess heat is removed from the liquid phase, which excess is partially formed due to mechanical energy dissipation in the circuit of circulating liquid phase, and partially due to steam condensation and to cooling of the uncondensed gas which is sucked off from the column 1 by the liquid-gas ejector 7, these providing the temperature stabilization.

At the output of the liquid-gas ejector, due to energy transmission from the active liquid phase to the passive vapour-gaseous phase coming via the mains 5 from the upper portion of the column 1, a two-phase mixture is formed having a pressure of greater than 0.11 MPa, which is fed to the saparator 8. The final condensation of the steam phase takes place in the mixture, which phase has not condensed in the flow-through part of the ejector. The mixture is divided in the separator 8 of the vacuum-creating device to form a gas and a liquid phases. The gas phase via the mains 11 is fed to the consumer's fuel system (not shown on the drawing). The liquid phase, partially refreshed with the liquid fraction (vacuum gas oil) from the column 1, is directed to the pump 9 input. The liquid phase excess formed due to condensed vapour delivered to the ejector 7 from the upper portion of column 1, as well as due to the flow via the mains 13 of the liquid fraction, is delivered via the mains 12 to the petroleum products receiver (not shown on the drawing). At the starting period of vacuum-creating device the working medium used is any fluid which is similar by its chemical and physical properties with the liquid phase, which phase is comprised of vapour condensate and the liquid fraction fed via the mains 3. But gradually the latter is replaced by the mixture of vapours condensate and of the liquid fraction accumulated in the separator 8. The mains 6 is used for discharge of the heavy fraction from vacuum distillation.

Thus, the suggested method and equipment for vacuum distillation of a liquid product suggest the solution of actual problems in petroleum refining industry: the ecologically friendly technology of vacuum petroleum refining is realized, financial expenses are reduced for obtaining vacuum in a column, the yield of light fractions is increased resulting from vacuum distillation of petroleum products.

Industrial Use

The given invention can be used for producing of a vacuum distillation product other than petroleum stock, for example, in chemical, food or pharmaceutical industries.

We claim:

1. A method of vacuum distillation of a petroleum product, said method comprising the following steps:
   feeding the petroleum product to a vacuum distillation column,
   separating the petroleum product in the column to a vapour-gaseous phase and at least one liquid fraction,
   feeding the vapour-gaseous phase into a vacuum-creating device comprising a liquid-gas ejector having an inlet in which a fluid working medium is supplied, condensing directly the vapour-gaseous phase in said vacuum-creating device, forming a two-phase mixture, separating the two phase mixture into a liquid phase and a gaseous phase, withdrawing the gaseous phase and portions of the liquid phase from the vacuum-creating device, forming the fluid working medium by combining a portion of the liquid phase with a portion of the at least one liquid fraction from the vacuum distillation column, wherein the portion of the liquid phase used as a working medium for the vacuum-creating device proceed with withdrawal therefrom of heat excess,.

delivering another portion of the at least one liquid fraction from the column back to an upper portion of the column, and delivering the fluid working medium by a pump to the inlet of the liquid-gas ejector of the vacuum-creating device.

2. An equipment for vacuum distillation of a petroleum product, said equipment comprising:

a vacuum distillation column, means for feeding the product and for removing at least one liquid fraction, means for supplying a portion of the at least one liquid fraction to the upper portion of the column, means for supplying a portion of the at least one liquid fraction to a vacuum-creating device, and means for removing a vapour-gaseous phase which connects the upper portion of said column with the vacuum-creating device, wherein said vacuum-creating device comprises a liquid-gas ejector, a gaseous-liquid separator for separating a gas from a two phase mixture arriving thereto, and a pump which are interconnected, wherein the gas inlet of the liquid-gas ejector is connected with the means for removing the vapour-gaseous phase, the liquid inlet of the liquid-gas ejector is connected with the pump output, the output of the liquid-gas ejector is connected with the inlet of the gaseous-liquid separator, and the liquid output of the gaseous-liquid separator is connected with the pump inlet.

3. The equipment according to claim 2, wherein said equipment further comprises a cooler mounted in the means between the liquid inlet of said liquid-gas ejector and the liquid output of said gaseous-liquid separator.

4. The equipment according to claim 2, wherein the means for removing the at least one liquid fraction from the column is connected with the gaseous-liquid separator.

* * * * *

UNITED STATES PATENT AND TRADEMARK OFFICE
CERTIFICATE OF CORRECTION

PATENT NO.    : 5,980,698
DATED         : November 9, 1999
INVENTOR(S)   : Abrosimov et al.

It is certified that error appears in the above-identified patent and that said Letters Patent is hereby corrected as shown below:

<u>Title page,</u>
Item [54], in the Title: after the word "product" and before the word "and" insert the words: -- PRESUMABLY OF PETROLEUM STOCK --

Signed and Sealed this

Twenty-third Day of July, 2002

Attest:

Attesting Officer

JAMES E. ROGAN
Director of the United States Patent and Trademark Office